(12) United States Patent
Cull et al.

(10) Patent No.: US 8,854,221 B2
(45) Date of Patent: Oct. 7, 2014

(54) SYSTEM TO IDENTIFY VISCOSITY OF ASPIRATED MATERIAL DURING OPHTHALMIC SURGERY

(75) Inventors: Laurence J. Cull, Woods Cross, UT (US); Carl C. Awh, Nashville, TN (US)

(73) Assignee: Bausch & Lomb Incorporated, Rochester, NY (US)

( * ) Notice: Subject to any disclaimer, the term of this patent is extended or adjusted under 35 U.S.C. 154(b) by 838 days.

(21) Appl. No.: 12/339,374

(22) Filed: Dec. 19, 2008

(65) Prior Publication Data
US 2010/0156646 A1    Jun. 24, 2010

(51) Int. Cl.
*G08B 21/00* (2006.01)
*A61M 1/00* (2006.01)
*A61F 9/007* (2006.01)

(52) U.S. Cl.
CPC .......... *A61F 9/00736* (2013.01); *A61M 1/0025* (2014.02); *A61M 1/0031* (2013.01); *A61M 2205/3331* (2013.01); *A61M 2210/0612* (2013.01)
USPC .............. 340/606; 340/611; 606/107; 604/19

(58) Field of Classification Search
USPC ......... 340/606–611; 606/107; 604/19, 22, 27, 604/28, 505
See application file for complete search history.

(56) References Cited

U.S. PATENT DOCUMENTS 6,599,277 B2    7/2003 Neubert .................... 604/317
6,945,981 B2 *  9/2005 Donofrio et al. .......... 606/169
2005/0245910 A1 * 11/2005 Wright et al. ................ 606/1
2007/0005030 A1 *  1/2007 Hopkins et al. ........... 604/317
2008/0208207 A1    8/2008 Huculak

FOREIGN PATENT DOCUMENTS

WO    WO 96/13216 A1    5/1996
WO    WO 02/26016 A2    4/2002
WO    WO 03/047653 A1   6/2003

OTHER PUBLICATIONS

International Search Report (PCTISA/210) and Written Opinion (PCT/ISA/237) mailed on Mar. 22, 2010.

* cited by examiner

*Primary Examiner* — Mohammad Ghayour
*Assistant Examiner* — Nay Tun
(74) *Attorney, Agent, or Firm* — Michael L. Smith

(57) ABSTRACT

An ophthalmic surgical system 10 detects a change in a viscosity of a material being aspirated from an eye 32. The system 10 includes a control module 18 connected to an aspiration pump 20, and a flow meter 19 connected to the control module 18 and the aspiration pump 20. The flow meter 19 provides a flow rate of material aspirated from the eye 32 by the aspiration pump 20. A surgical handpiece 24 connected to the aspiration pump 20 and the control module 18 is inserted into the eye 32 during surgery. The control module 18, during surgery, detects a step change in the flow rate of material aspirated from the eye 32 and the control module 18 further causes the surgical system 10 to alert a surgeon that a change in viscosity of the material being aspirated has been detected indicating that the handpiece 24 has moved from a material of a first viscosity to a material of a second viscosity.

11 Claims, 2 Drawing Sheets

SYSTEM TO IDENTIFY VISCOSITY OF ASPIRATED MATERIAL DURING OPHTHALMIC SURGERY

BACKGROUND OF THE INVENTION

1. Field of the Invention

The present invention is related to detecting a flow of tissue and fluid aspirated from an eye. More specifically, the present invention is related to detecting a difference in viscosity between different materials being aspirated.

2. Description of the Related Art

During Ophthalmic Surgery both anterior and posterior surgery various materials, some transparent, are removed from an eye by aspiration, while other transparent materials are simultaneously infused into the eye. In anterior surgery the materials removed include a cataractous or clear lens, vitreous, cortical material and the infused material includes balanced-salt-solution (BSS) and viscoelastic. BSS and viscoelastic are infused to ensure that the eye stays inflated as an eye collapse during surgery can lead to catastrophic results. Posterior surgery material removed includes vitreous humor (vitreous), which is a clear gel filling the space between the lens and retina.

It is often difficult to distinguish between the various materials being removed because there is little visual difference between the different materials, except in the case of cataracts, which are easily identified. Also, a surgeon's ability to visualize the materials can be compromised by the eye's anatomy and inadequate illumination and magnification. The inability to distinguish between the materials being removed can lead to wasted time removing fluids infused into the eye, rather than removing the targeted natural tissue. This is especially true in posterior surgery during vitrectomy, where significant time can be spent removing BSS to ensure that all the vitreous is removed prior to operating on the diseased or torn part of the retina.

One difference between BSS and vitreous is the viscosity, where BSS is water and vitreous is a much more viscous gel.

Therefore, it would be desirable if there were a feedback mechanism or alert that could inform a surgeon when the instrument removing material from the eye encounters a different material, particularly when a change in viscosity of the removed material is encountered.

DETAILED DESCRIPTION

Figure 1:
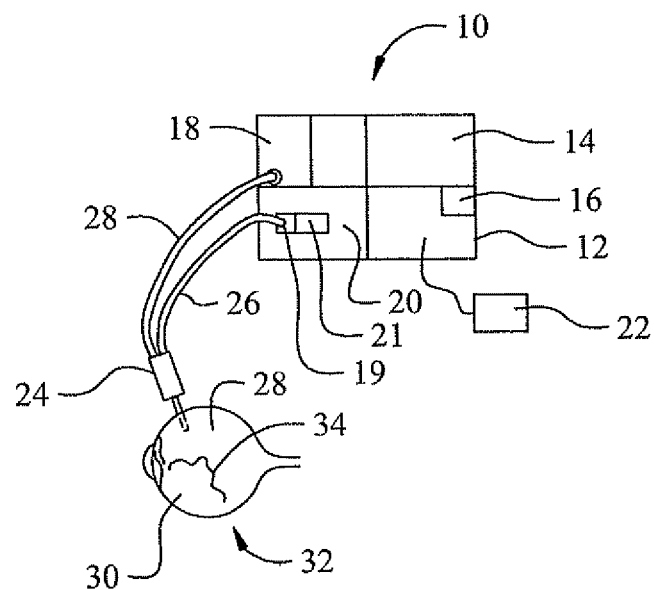
FIG. 1 is a graphical illustration of an ophthalmic surgical system in accordance with the present invention.

FIG. 1 is an illustration of an ophthalmic surgical system, in accordance with the present invention. A surgical system 10 includes a console 12 preferably having a display 14, an audio source 16, a control module 18, and an aspiration pump 20. System 10 may also include a foot controller 22, for controlling various surgical parameters and devices.

The following description concentrates on an example of posterior vitrectomy surgery, but those skilled in the art will understand that the present invention equally applies to other types of ophthalmic procedures, including anterior surgery where it would be helpful to alert a surgeon when a change in material being aspirated is detected, such as when viscoelastic is being aspirated.

During surgery a vitreous (vit) cutter 24 is used to remove the gelatinous vitreous humor. The vit cutter 24 severs the vitreous that is pulled into the cutter via vacuum generated by pump 20, which also includes a flow meter 19 associated with a collection cassette 21. The severed tissue is aspirated to the collection cassette 21, via tubing 26, while the speed, duty cycle, and stroke are controlled by module 18 via line 28.

In the development of a vacuum based flow aspiration system, details of which are described in U.S. Pat. No. 6,599,277 (Ser. No. 09/997,883), filed Nov. 30, 2001, entitled Aspiration Flow Meter and Control, U.S. patent application Ser. No. 11/957,841, filed Dec. 17, 2007, entitled Recessed Electrodes for Sensing Flow in Ophthalmic Surgery System, and U.S. patent application Ser. No. 12/270,209, filed Nov. 13, 2008, entitled Air Filter for Ophthalmic Surgical System, all of which are incorporated by reference, it was discovered that the flow meter described in the above patent and patent applications exhibited a clearly identifiable step response when the tip of the vit cutter 24 moved from BSS to vitreous in testing. Flow meter 19, as disclosed and described in the above cited patent and patent applications, is preferably an electro-magnetic flow sensor with electrodes exposed to a flow stream of aspirated tissue and fluids.

Using FIG. 1 to illustrate this observation, when the tip of vit cutter 24 moves from BSS 28 to vitreous 30, in eye 32, a step response in the flow meter 19 associated with pump 20 is easily detected. Since both BSS 28 and vitreous 30 are transparent line 34 is used to show the boundary between BSS 28 and vitreous 30.

The step response to flow rate is directly related to the viscosity of the material contacted by the vit cutter 24 (or other instrument, such as a phacoemulsification device, for other types of surgery). The detection of this change in viscosity can be used to provide a surgeon real-time, essentially instantaneous feedback or notice that the vit cutter is cutting vitreous or simply aspirating BSS. Some surgeons find it difficult to know if they have the vit cutter in vitreous or BSS because there is little visual distinction between the two materials. Consequently surgeons can waste time needlessly aspirating BSS to be sure they have excised all the vitreous. Therefore, the present invention, upon detecting a step change in flow rate provides the surgeon an alert that the vit cutter has contacted a material of different viscosity. This alert can take several forms, some of which include a visual or graphical alert or warning on display 14, an audible alert from source 16 or a combination of both. The alert can simply be an icon or tone or it could be a written or verbal alert. In addition, the alert can simply indicate that a change in viscosity has been detected or it can be more specific and alert the surgeon that the vit cutter has moved from BSS to vitreous or vice versa.

Further, the notice could take the form of tactile feedback through a vibration or the like in the vit cutter or foot controller. This could take the form of a piezo vibration circuit 38 in a surgical handpiece 36, shown in FIG. 2. Handpiece 36 is shown as a vit cutter but could be another type of surgical instrument. Control module 18, upon detecting a step response change in flow meter 19 will send a signal to handpiece 36 causing circuit 38 to vibrate and alert the surgeon that handpiece 36 is now aspirating a material of different viscosity.

Figure 2:
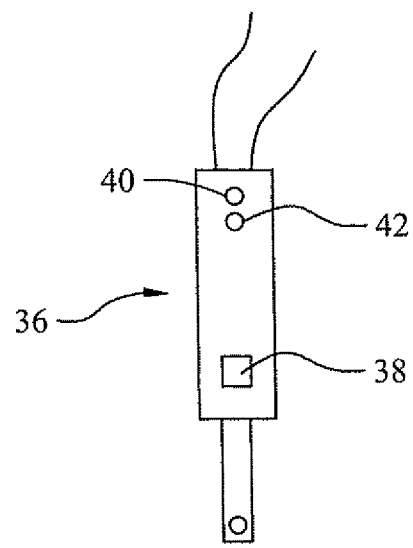
FIG. 2 is an elevation view of a surgical handpiece to be used with an embodiment of the present invention.

A visual feedback could also be provided on the vit cutter or other surgical handpiece through different colored LEDs 40 and 42, shown in FIG. 2. An example is that LED 40 is red and indicates only BSS is being aspirated and LED 42 is green indicating that vitreous is being cut and aspirated.

The step response detected was found to be on the order of a 10% or more change in the flow rate for the flow meter 19 used. The flow rate dropped when the tip moved from BSS to vitreous and similarly increased when the tip moved from vitreous to BSS. Said another way, when the tip crosses boundary line 34 the step response is detected. This step response in flow rate is recognized, essentially instantaneously (less than one second), by the flow meter even though the flow meter is physically connected to the flow path several feet from the tip of the vit cutter. This very rapid response in flow rate change was due to the flow meter 19. If a less responsive flow meter were to be used, the present invention would still provide useful information to a user, only in a less timely manner. The time response of the flow meter used is directly related to the efficiency of the warning that can be given to a user. A less responsive sensor than flow meter 19 would simply mean that a surgeon may have wasted the lag in response time removing BSS instead of the intended vitreous.

Figure 3:
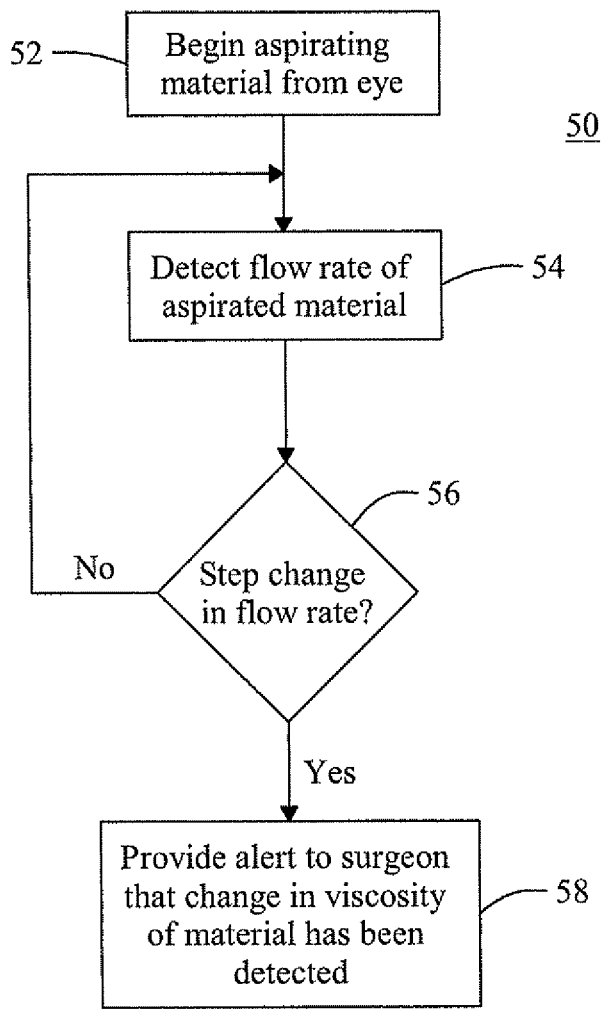
FIG. 3 is a logic flow chart of a method in accordance with the present invention.

FIG. 3 sets forth a logic flow chart 50 of a method to be used during surgery to alert a surgeon that a change in viscosity has been detected because the surgical handpiece being used has moved from a material of a first viscosity to a material of a second viscosity.

Step 52 determines that system 10, and specifically pump 20 has begun aspirating material from eye 32. At step 54, flow meter 19 associated with pump 20 detects a flow rate of aspirated material from eye 32 through surgical handpiece 24. The control module 18 then determines, at step 56, if a step change in flow rate has been detected.

If, at step 56, a step change in flow rate is not detected the system 10 loops back to step 54 and continues to detect the flow rate. If, at step 56, a step change is detected, control module 18 causes system 10 to provide an alert to the surgeon that a change in viscosity of material being aspirated has been detected. As outlined above the alert can be more specific in that the alert can tell or inform the surgeon if he has just moved from vitreous to BSS or vice versa.

Thus, there has been described a system and method of detecting and alerting a surgeon to a step change in the flow rate of material being aspirated from an eye. By implementing the teaching described above a number of benefits can be attained, including avoiding any confusion or doubt about whether vitreous or BSS is being aspirated.

We claim:

1. An ophthalmic surgical system for detecting a change in a viscosity of a material being aspirated from an eye, comprising:
   at least a control module connected to an aspiration pump, and a flow meter connected to the control module and the aspiration pump, the flow meter for providing a flow rate of material aspirated from the eye by the aspiration pump;
   a surgical handpiece connected to the aspiration pump and the control module to be inserted into the eye during surgery; and
   wherein the control module, during surgery, detects a step change in the flow rate of material aspirated from the eye and the control module, based only on the detected step change without the use of any data stored in the control module prior to surgery, further causes the surgical system to alert a surgeon that a change in viscosity of the material being aspirated has been detected indicating that the handpiece has moved from a material of a first viscosity to a material of a second viscosity.

2. The system of claim 1 wherein the system further includes a display for providing a visual alert to the surgeon.

3. The system of claim 1 wherein the system further includes an audio source for audibly alerting the surgeon.

4. The system of claim 1 wherein the system further includes a foot controller for providing tactile feedback of the alert to the surgeon.

5. The system of claim 1 wherein the surgical handpiece includes a vibration circuit for providing tactile feedback of the alert to the surgeon.

6. The system of claim 1 wherein the surgical handpiece includes visual feedback of the alert to the surgeon.

7. The system of claim 1 wherein the alert further indicates, upon the detection of the change in viscosity, whether the handpiece has moved from the material of the first viscosity to the material of the second viscosity or vice versa.

8. The system of claim 7 wherein the material of the first viscosity is balanced-salt-solution and the material of the second viscosity is vitreous.

9. A method of alerting a surgeon when a viscosity of material being aspirated through a surgical handpiece has been detected, the method comprising the steps of:
   aspirating material from an eye with an aspiration pump;
   detecting a flow rate of the aspirated material with a flow meter associated with the aspiration pump;
   determining if a step change in the flow rate has been detected with a control module connected to the flow meter;
   providing an alert to the surgeon, based only on when the detected step change in the flow rate has been detected without the use of any data stored in the control module prior to surgery, that a change in viscosity of the material being aspirated has been detected.

10. The method of claim 9 wherein the step of providing the alert is provided by one or more of a display, an audio source, the surgical handpiece, and a foot controller.

11. The method of claim 9 wherein the step of providing the alert includes informing the surgeon whether the surgical handpiece has moved from a material of a first viscosity to a material of a second viscosity or vice versa.

\* \* \* \* \*